United States Patent
Chaffringeon

[11] Patent Number: 5,830,199
[45] Date of Patent: Nov. 3, 1998

[54] DISPOSABLE DEVICE FOR RECOVERY, AND IF APPROPRIATE ANALYSIS, OF A BODY FLUID

[76] Inventor: Bernard Chaffringeon, La Logere, F-69480 Anse, France

[21] Appl. No.: 687,383

[22] PCT Filed: Mar. 29, 1995

[86] PCT No.: PCT/FR95/00402

§ 371 Date: Sep. 26, 1996

§ 102(e) Date: Sep. 26, 1996

[87] PCT Pub. No.: WO95/26161

PCT Pub. Date: Oct. 5, 1995

[30] Foreign Application Priority Data

Mar. 29, 1994 [FR] France .................................. 94 04066

[51] Int. Cl.⁶ .................................................. A61M 1/00
[52] U.S. Cl. .......................... 604/327; 600/574; 600/582
[58] Field of Search .................................. 128/760, 761, 128/769, 771; 604/327–331, 349, 352, 350; 600/573, 574, 582, 584

[56] References Cited

U.S. PATENT DOCUMENTS

| | | | |
|---|---|---|---|
| 3,651,810 | 3/1972 | Ormerod | 604/329 |
| 3,683,914 | 8/1972 | Crowley | 604/329 |
| 3,958,561 | 5/1976 | Bucalo | 604/330 |
| 5,125,118 | 6/1992 | Green | 128/761 |
| 5,231,992 | 8/1993 | Leon . | |

FOREIGN PATENT DOCUMENTS

| | | |
|---|---|---|
| 0101981 | 3/1984 | European Pat. Off. . |
| 3327444 | 2/1984 | Germany . |
| 3327967 | 2/1985 | Germany . |
| WO 92/21774 | 12/1992 | WIPO . |

*Primary Examiner*—Robert A. Clarke
*Attorney, Agent, or Firm*—Oliff & Berridge, PLC

[57] ABSTRACT

Disposable device for recovery, and if appropriate analysis, of a body fluid, said device comprising:

a relatively rigid conduit element directly in contact with the inner wall of an elongate intra-corporeal cavity, having an open end or neck, and a closed end or base, and the outer surface of which is biocompatible with the inner wall of said intracorporeal cavity;

a collection means for collecting the body fluid, mounted or integrated inside the conduit element, facing the neck of the conduit element, at an outlet, facing the base of the conduit element;

a nonreturn means for the body fluid which has been collected, closing the outlet of the collection means of the conduit element, in the direction counter to that of collection.

20 Claims, 1 Drawing Sheet

DISPOSABLE DEVICE FOR RECOVERY, AND IF APPROPRIATE ANALYSIS, OF A BODY FLUID

BACKGROUND OF THE INVENTION

The present invention relates to the recovery, and if appropriate the analysis, of a body fluid directly from an elongate intracorporeal cavity, and by way of a non-limiting example the present invention will be introduced, defined and explained with reference to the recovery of the cervical mucosa in the vaginal cavity of women for detection of the period of fertility.

In order to determine the periods of fertility in women, it is known, and it has been proposed, to detect and monitor the presence and/or concentration of certain biochemical or biological constituents of said mucus, such as a peroxidase or a compound having a peroxidase activity, or such as a mucopolysaccharide or a glycoprotein, by using reagents or colored reagent systems, for example, in the former case, an oxidation-reduction compound, of which at least the oxidized form is colored, for example guaiacol, and in the latter case safranin.

The solutions which have been proposed for the use of such reagents or reactive systems have generally been rudimentary and have in practice been difficult for women to put into use, namely:

taking a sample of the cervical mucus in situ, with an element capable of recovering the mucus, such as a swab, then bringing said element into contact, outside the vaginal cavity, with the reagent in liquid form;

introducing into the vaginal cavity an absorbent tampon impregnated with the reagent, and withdrawing said tampon after a certain time, and observing the color, or the change of color, of the reagent on the absorbent tampon.

All these relatively rudimentary solutions are not adapted to an everyday use consistent with the personal hygiene practices of women.

As regards taking samples of body fluids or secretions, independently of their biochemical or biological analysis subsequent to or concomitant with the sampling, there are, in brief, two types of solution currently envisaged.

The first consists in recovering said fluids or secretions extracorporeally, at the actual site of their excretion, or in the vicinity of said site, on any suitable support or means for recovery. A solution of this kind has been described in DE-A-33 27 444, wherein a urine recovery device is disclosed, said device being provided with lips to sealingly surround the feminine urethral meatus, and comprising collection means for the body fluid and nonreturn means to prevent the collected liquid from leaking out from the collection means. However, this solution appears inappropriate when the fluid or secretion remains to all intents and purposes inside the body, such as the cervical mucus inside the vagina.

The second consists in recovering said fluids or secretions intracorporeally, within the intracorporeal cavity itself. This presupposes the use of devices or means for recovery which are adapted to be introduced into, kept inside, and withdrawn from the intracorporeal cavity. At present, the devices which are on the market or are described in the available literature are essentially adapted for the recovery of cells or cell samples.

SUMMARY OF THE INVENTION

The subject of the present invention is a disposable device, of the intracorporeal type, which is adapted specifically for the collection of body fluids or liquids.

The device according to the invention comprises in a general manner, collection means for recovering a body liquid, mounted or integrated into the device, extending along the length of the latter, and nonreturn means for the collected body liquid, said means closing the collection means when the liquid flows in the device in an opposite direction to that of collection, and further comprising a relatively rigid conduit element, adapted in shape and dimensions to be fitted and held directly in contact with the inner wall of an elongate intracorporeal cavity, having a first open end, termed the neck, and a second closed end, termed the base; this conduit element is sufficiently stiff along its length to be pushed via its base, by any suitable means, including manually, and thereby introduced via its neck into the intracorporeal cavity for recovery purposes; and the structuring or the materials of the outer surface of the conduit element are chosen to be, or to remain, biocompatible with the inner wall of the intracorporeal cavity;

the collection means for collecting the body fluid are mounted or integrated inside the conduit element, and extend along the length of the latter, from an inlet of relatively large cross section, facing or at the level of the neck of said conduit element, to an outlet of relatively small cross section, facing or opposite the base of same conduit element;

the nonreturn means for the body fluid which has been collected close the outlet of relatively small cross section, when fluid collected flows in said conduit element, in the direction opposite to that of collection.

The term "biocompatible" refers to the fact that the contact between the outer surface of the conduit element and the wall of the intracorporeal cavity does not generate any adverse biological reaction, for example of the toxic or allergic type.

In the case of a device according to the invention, which is adapted for the recovery of the cervical mucus in the vaginal cavity, a solution is obtained which requires, for its implementation, the same maneuvers which are necessary for personal hygiene in women.

Preferably, and when the collection device serves at the same time and directly as a reaction device, a reaction means is arranged inside the conduit element, at its base, facing the outlet of the collection means, and comprises at least one reagent, for example deposited on an absorbent layer, capable of reacting with at least one component of the body fluid which is recovered, in order to give at least one reaction product, especially colored, revealing the presence of said component in said body fluid.

In this case, the base of the conduit element is preferably transparent, and the reagent is arranged against this base, and in fact facing the outlet of the collection means, in such a way that when the reaction product is colored, this color or absence of color can be seen or visualized by the user.

The recovery device according to the invention, as described above, can therefore be used directly, in particular without subsequent addition of color reagent or developer by the user, and in this latter case the color reaction is observed immediately after the removal of the device.

BRIEF DESCRIPTION OF THE DRAWINGS

The present invention is now described with reference to the attached drawing, in which.

DESCRIPTION OF PREFERRED EMBODIMENTS

Figure 1:
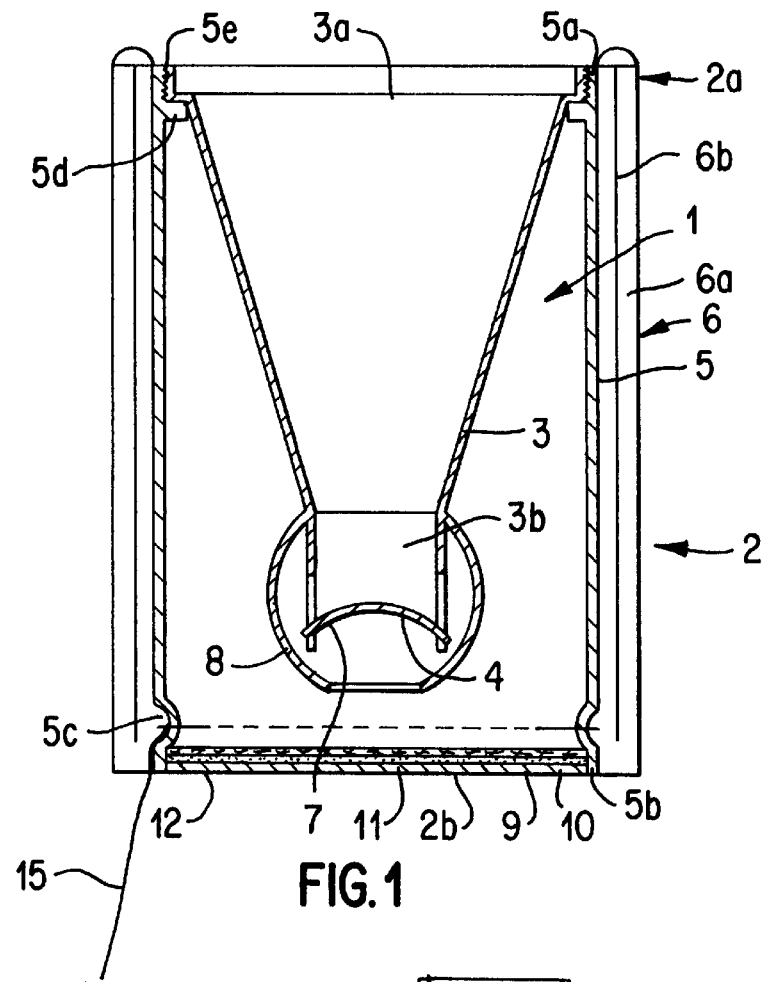
FIG. 1 represents a cross section of a disposable device according to the invention.

In a general manner, a disposable device 1 for recovery of body fluid, for example cervical mucus, directly from an elongate intracorporeal cavity, for example the vaginal cavity, comprises:

a conduit element 2 adapted in shape and dimensions to be fitted and held in contact with the inner wall, by simple constriction, of the intracorporeal cavity, having an open end or neck 2a, and a closed end or base 2b; this element is in itself sufficiently stiff or relatively rigid along its length to be pushed via its base 2b, and thereby introduced via its neck 2a into the intracorporeal cavity; and in a general manner, as described hereinafter, its outer surface is chosen to be biocompatible with the inner wall of the intracorporeal cavity;

a collection means 3 for collecting the body fluid, mounted in a removable manner or integrated inside the conduit element 2, extending along the length of the latter, from an inlet 3a of relatively large cross section, at the level of the neck 2a of the conduit element 2, to an outlet 3b of relatively small cross section, facing, but at a spacing from, the base 2b of the conduit element 2;

a nonreturn means 4 for the body fluid which has been collected, closing the outlet 3b of the collection means when the fluid collected flows into the conduit element 2, in the direction counter to that of the collection.

The conduit element 2 can have a composite structure and can comprise a relatively rigid tube 5, for example made of transparent plastic material, with a neck 5a and a base 5b on which is fitted, if appropriate, a biocompatible sleeve 6 surrounding at least the side wall of the tube, consisting for example of an outer tube 6a made of materials of natural origin, such as cellulose or cotton, and a rigid inner matrix 6b made of polymer as a support for said second tube, whose anterior edge (in the direction of introduction of the device) is rounded, and whose posterior edge is straight.

The collection means 3 and its nonreturn means 4 are mounted in a removable manner, or fixed manner, in relation to the conduit element 2, and more precisely in relation to the rigid tube 5, by virtue of a screw pitch 5e and a shoulder 5d which are provided on the tube 5 at the level of its neck 5a.

The nonreturn means 4 comprises a valve device 7 mounted in a movable manner, or on an openworked support, with respect to the outlet 3b of the collection means 3, held against this outlet in the direction counter to that of the collection of the body fluid, the whole unit being arranged in a collector 8 for said fluid, opposite the base 2b of the conduit element 2.

A removal line 15 in the form of a thread or cord is fixed to the conduit element 2, on the side of its base 2b, by way of a groove 5c provided in the tube 5.

A reaction means or system 9 is arranged inside the conduit element 2, at its base 2b, facing the outlet 3b of the collection means 3, and incorporates at least one reagent, and if appropriate a fluidizing agent for the cervical mucus, deposited for example either directly or on an absorbent layer 12, capable of reacting with at least one component of the body fluid which has been collected, in order to give at least one color reaction product, revealing the presence of said component in the body fluid. As has already been mentioned, the color reagent on its absorbent support is arranged against the base 2b, facing the outlet 3b of the collection means 3, and more precisely against the transparent base wall 10 of the tube 5. The layer impregnated with reagent 9 is covered by a web 11 which is semipermeable, in the sense that it is permeable with respect to the collected body fluid in the direction of collection, while it holds back this same fluid in the other direction. This web can also be impregnated with the fluidizing agent for the cervical mucus in the case where the device is to be used for analyzing the latter, said agent promoting the passage of the compounds which are to be detected and being, for example, a surface-active agent.

In a general manner, although not represented in FIG. 1, the shape and the dimensions of the conduit element 2 are adapted to those of the vaginal cavity.

Figure 2:
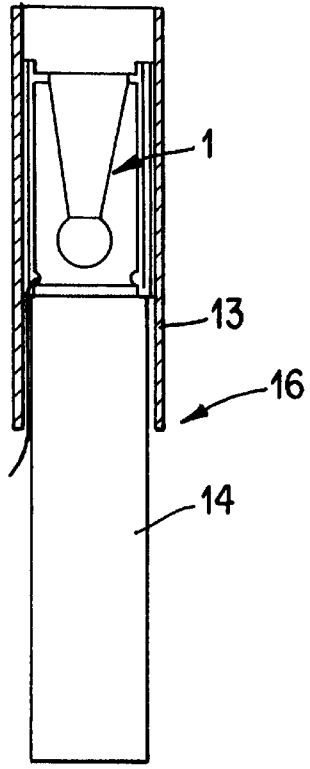
FIG. 2 represents an assembly ready for use, comprising a device according to FIG. 1 together with an applicator system.

In accordance with FIG. 2, the device described above can form part of a ready-to-use assembly comprising this same device 1 and an applicator system 16. The latter comprises a guide tube 13, inside which the recovery device 1 is inserted, and a pusher 14 housed inside the guide tube, abutting against the recovery device. Such a system can be introduced directly into the intracorporeal cavity, for example the vaginal cavity, and by pushing the pusher the recovery device is released from the applicator system, in order to position said device in this same cavity.

The recovery device can be used not only for the detection of a component in a body fluid, but also for detecting any chemical, biochemical or biological state of this same body fluid, for diagnostic, prophylactic or therapeutic purposes. This means that this recovery device can incorporate very different reagents or reaction systems, of a purely chemical type, for example enzymatic, or biological, for example an antigen or an antibody.

Consequently, a recovery device according to the invention can have very broad applications, among which there may be mentioned:

the detection of a hormone, and in particular of a hormonal peak;

the sampling and the histological and/or cytochemical analysis of a body fluid, in particular for detecting pathological conditions, or for demonstrating certain physiological phases of a natural cycle, for example of a hormonal cycle.

The following reagents will be mentioned in particular, by way of example, for the detection of a glycoprotein or of a mucopolysaccharide, and consequently of the fertile period in women: safranin, toluidine blue O, Alcian blue, trypan blue, a tolonium salt, PAS (periodic acid-Schiff), or a mixture of these, if appropriate combined with an agent promoting the color reaction, such as polyvinylpyrrolidone. against the recovery device. Such a system can be introduced directly into the intracorporeal cavity, for example the vaginal cavity, and by pushing the pusher the recovery device is released from the applicator system, in order to position said device in this same cavity.

The recovery device can be used not only for the detection of a component in a body fluid, but also for detecting any chemical, biochemical or biological state of this same body fluid, for diagnostic, prophylactic or therapeutic purposes. This means that this recovery device can incorporate very different reagents or reaction systems, of a purely chemical type, for example enzymatic, or biological, for example an antigen or an antibody.

Consequently, a recovery device according to the invention can have very broad applications, among which there may be mentioned:

the detection of a hormone, and in particular of a hormonal peak;

the sampling and the histological and/or cytochemical analysis of a body fluid, in particular for detecting pathological conditions, or for demonstrating certain physiological phases of a natural cycle, for example of a hormonal cycle.

The following reagents will be mentioned in particular, by way of example, for the detection of a glycoprotein or of a mucopolysaccharide, and consequently of the fertile period in women: safranin, toluidine blue O, Alcian blue, trypan blue, a tolonium salt, PAS (periodic acid-Schiff), or a mixture of these, if appropriate combined with an agent promoting the color reaction, such as polyvinylpyrrolidone.

What is claimed is:

1. A disposable device for recovery of a body fluid, said device comprising collection means for recovering a body liquid, extending along the length of the device, and non-return means for the collected body liquid, said means closing the collection means when the liquid flows in the device in an opposite direction to that of collection, wherein:

the device comprises a relatively rigid conduit element, adapted in shape and dimensions to be fitted and held directly in contact with the inner wall of an elongate intra-corporeal cavity in the intracorporeal cavity, having an open end or neck, and a closed end or base, and is sufficiently stiff along its length to be pushed via its base, and introduced via its neck, into said intracorporeal cavity, and the outer surface of which is biocompatible with the inner wall of said intracorporeal cavity;

the collection means for collecting the body fluid is mounted or integrated inside the conduit element, extending along the length of the latter, from an inlet of relatively large cross section, facing the neck of the conduit element, to an outlet of relatively small cross section, facing the base of the conduit element;

the nonreturn means for the body fluid, which has been collected, closes the outlet of relatively small cross section when said fluid flows in the conduit element, in the direction counter to that of collection.

2. The device as claimed in claim 1, wherein the conduit element comprises a relatively rigid tube with a neck and a base.

3. The device as claimed in claim 2, wherein the conduit element further comprises a biocompatible sleeve surrounding at least the side wall of said tube.

4. The device as claimed in claim 1, wherein the collection means and its nonreturn means are mounted in a removable manner in relation to the conduit element.

5. The device as claimed in claim 1, wherein the nonreturn means comprises a valve device mounted movably with respect to the outlet of the collection means, held against said outlet in the direction counter to that of the collection of the body fluid.

6. The device as claimed in claim 5, wherein the valve device is arranged in a collector for said fluid.

7. The device as claimed in claim 1, wherein a removal line is fixed to the conduit element, on the side of its base.

8. The device as claimed in claim 7, wherein the removal line is fixed to the conduit element in a groove.

9. The device as claimed in claim 1, wherein a reaction means is arranged inside the conduit element, at its base, facing the outlet of the collection means, and said reaction means comprises at least one reagent capable of reacting with at least one component of the body fluid, or in the presence of a biological or biochemical state of said fluid, in order to give at least one reaction product, revealing the presence of said biological or biochemical state, or of said component in said body fluid.

10. The device as claimed in claim 9, wherein the reaction product is colored, the base is transparent, and the reagent is arranged in a relatively thin layer against the base, facing the outlet of the collection means.

11. The device as claimed in claim 10, wherein the layer of reagent is covered by a semipermeable web, which is permeable with respect to the body fluid in the direction of collection, and holds back said fluid in the other direction.

12. The device as claimed in claim 11, wherein at least one of the web and the layer is impregnated with a fluidizing agent promoting the passage of the compounds which are to be detected.

13. The device as claimed in claim 9, wherein a reaction means is deposited on an absorbent layer.

14. The device as claimed in claim 9, wherein said at least one reaction product is colored.

15. The device as claimed in claim 1, wherein the shape and the dimensions of the conduit element are adapted to those of the vaginal cavity, and the body fluid comprises the cervical mucus.

16. The device as claimed in claim 15, wherein the component of the cervical mucus whose presence is being tested for is a peroxidase component, and the reagent is an oxidation- reduction compound, of which at least the oxidized form is colored.

17. The device as claimed in claim 16, wherein said reagent is guaiacol.

18. The device as claimed in claim 15, wherein the component of the cervical mucus whose presence is being tested for is a mucopolysaccharide or a glycoprotein, and the reagent is selected from the group consisting of safranin, toluidine blue O, Alcian blue, trypan blue, a tolonium salt, PAS (periodic acid-Schiff), and a mixture of these.

19. An assembly ready for use and comprising a device as claimed in claim 1 and an applicator system.

20. The assembly as claimed in claim 19, wherein the applicator system comprises a guide tube inside which the recovery device is inserted, and a pusher housed inside the guide tube, abutting against the recovery device.

* * * * *